United States Patent [19]

Lehman de Gaeta et al.

[11] Patent Number: 5,424,394
[45] Date of Patent: Jun. 13, 1995

[54] SYNTHETIC PREPARATION OF AMYLIN AND AMYLIN ANALOGUES

[76] Inventors: Laura S. Lehman de Gaeta, 8126 Camino del Sol, La Jolla, Calif. 92037; Elisabeth Albrecht, 10540 Bannister Way, San Diego, Calif. 92126

[21] Appl. No.: 90,361

[22] Filed: Jul. 8, 1993

Related U.S. Application Data

[63] Continuation of Ser. No. 962,617, Oct. 16, 1992, abandoned, which is a continuation of Ser. No. 667,040, Mar. 8, 1991, abandoned.

[51] Int. Cl.⁶ .................. A61K 38/00; A61K 38/23; A61K 37/00; C07K 14/00
[52] U.S. Cl. ........................... 530/324; 530/307; 530/327
[58] Field of Search .............. 530/324, 327, 307; 514/12

[56] References Cited

U.S. PATENT DOCUMENTS

| | | | |
|---|---|---|---|
| 4,743,677 | 5/1988 | Noda et al. | 530/307 |
| 4,992,530 | 2/1991 | Morita et al. | 530/307 |
| 5,367,052 | 11/1994 | Cooper et al. | 530/307 |

FOREIGN PATENT DOCUMENTS

0309100  3/1989  European Pat. Off. .
9006936  6/1990  WIPO .

OTHER PUBLICATIONS

Leighton & Cooper, Nature 335:632–635 (1988).
Leighton et al., Diabetologia 31:513A (1988).
Fujii et al., Chem. Pharm. Bull. 35(6):2339–2347 (1987).
Fujii et al., Chem. Pharm. Bull. 35(12):4769–4776 (1987).
Cooper et al. PNAS USA vol. 85, 7763–7766 (Oct. 1988).
Hiskey, *The Peptides,* vol. 3 (Gross & Meinhofer ed. 1981) pp. 137–167.

*Primary Examiner*—Jill Warden
*Assistant Examiner*—Benet Prickril

[57] ABSTRACT

Synthetic amylin and amylin analogs which have high biological activity and which are substantially free from deletion peptides and other contaminating peptides are provided. Also provided are methods for the solid phase peptide synthesis of amylin and amylin analogs.

12 Claims, 1 Drawing Sheet

SYNTHETIC PREPARATION OF AMYLIN AND AMYLIN ANALOGUES

This is a continuation of application Ser. No. 07/962,617, filed Oct. 16, 1992, now abandoned, which is a continuation of application Ser. No. 07/667,040, filed Mar. 8, 1991, now abandoned.

FIELD OF THE INVENTION

The field of the invention is biology and peptide chemistry and, more particularly, the biology and biochemistry of peptides related to energy metabolism and diabetes. The present invention relates to the preparation by solid state peptide synthesis of amylin and amylin analogs having high purity and high biological activity.

BACKGROUND AND INTRODUCTION TO THE INVENTION

Amylin is a newly discovered 37-amino acid peptide which was first isolated from islet amyloid found in the pancreases of human patients with non-insulin dependent diabetes mellitus (NIDDM), also known as Type II diabetes. (Cooper et al., Biochem. Biophys. Acta. 1014:247-258 (1989); Cooper et al., Proc. Nat'l. Acad. Sci. USA 84:8628-8632 (1987)). Islet $\beta$-cells cosecrete amylin and insulin in response to glucose and amino acids. (Ogawa et al., J. Clin. Invest. 85:973-976 (1990)). We have discovered that amylin and insulin together regulate carbohydrate metabolism in vitro and in vivo. Administration of amylin can prevent the primary occurrence of insulin-induced hypoglycemia in normal people. Inappropriate production of amylin can lead to diabetes. For instance, it has been reported that animals which model the NIDDM disease state demonstrate over-production of amylin at the transcriptional level. (Jamal et al., J. Endocrinol. 126:425-429 (1990).

Insulin-dependent diabetes mellitus (IDDM) patients suffer from autoimmune destruction of pancreatic $\beta$-cells resulting in the reduction of insulin production which, in turn, causes hyperglycemia. A serious side-effect of insulin therapy for IDDM patients is hypoglycemia which is made more severe by the absence of amylin due to autoimmune destruction of the islet $\beta$-cells. Evidence has been collected which confirms differences in the circulating blood levels of amylin in Type I diabetics, persons with obesity and impaired glucose tolerance, and normal people. (Ludvik, et al., Diabetes 39 Supp. 1, 116A (1990); Harttner, E., et al. Lancet, 1990, 854; Harttner, E., et al., Lab. Med. 14:229 (1990)). Because amylin has been reported to play a pivotal role in diabetes and other insulin resistant states, there has been a need to generate synthetic amylin in order to be able to further investigate its physiological properties.

Fully active human amylin contains an internal disulfide bond and a C-terminal amide group. Although the amino acid sequence is reported to be well conserved in a number of species, the physical properties of individual amylins have been found to vary depending on the source. (Cooper, G. J. S., et al., Proc. Nat'l. Acad. Sci. USA 84:8626-8632 (1987); Leffert, J. D. et al. Proc. Nat'l. Acad. Sci. USA 86:5738-5742 (1989); Nishi, M. et al. Proc. Nat'l. Acad. Sci. USA 86:3127-3130 (1989)). For instance, amyloid formation, which is characterized by an abnormal aggregation of peptide, is observed with human and feline amylin but not with the rodent analogs. (Nishi, M., et al., Proc. Nat'l. Acad. Sci. USA 86:3127-3130 (1989)).

Although the biological activity of amylin has been examined with natural material isolated from human pancreatic islet amyloid (Leighton, B. and Cooper, G. S. S., Nature, 335:632-635 (1988)), most studies have used amylin produced by solid phase peptide synthesis. There exist several publications which report a failure to demonstrate certain previously observed or predicted biological activities of amylin (Bretherton-Watt, D., et al., Diabetologia 33:115-117 (1990); Ghatei, M. A., et al. J. Endocrinol. 124:R9-R11(1990)). Attempts at synthesis of human amylin by synthetic methods have also resulted in preparations which are widely variable with respect to chemical purity as well. Such preparations have been contaminated by deletion peptides formed during the process of chemical synthesis. In order to be able to perform further studies examining the biological activities of amylin and reliable quantitative studies with synthetic human amylin, sufficient amounts of peptide of adequate purity and biological activity and which may be standardized (with respect to both purity and activity) are needed.

Experiments designed to examine the biological activities of human amylin in which previously available preparations of peptide were employed must include an evaluation of the chemical and biological variability of those preparations. The contamination of these amylin preparations with peptides of unknown, and possibility deleterious, activities will impede in vivo studies with these peptides, especially in humans.

SUMMARY OF THE INVENTION

The present invention is directed to methods for the preparation of amylin and amylin analogs by solid phase peptide synthesis and to the synthetic amylin and amylin analogs produced thereby.

According to the present invention, we have developed methods for the efficient synthesis of amylin and amylin analogs which result in peptides of high purity which are substantially free of deletion peptides and other contaminating peptides and which show reproducibly high biological activity as measured by assays of its ability to cause resistance to insulin in vitro by inhibiting insulin-stimulated incorporation of labelled glucose into glycogen in isolated rat soleus muscle. (Leighton, B. and Cooper, G. J. S., Nature 335:632-635 (1988). These peptides have been demonstrated to be at least about 95 percent pure as measured by analytical reversed phase HPLC after purification by extraction from resin support and preparative reversed phase HPLC.

Quantitative ninhydrin analyses which are used to measure coupling efficiencies have confirmed the identification of inefficient coupling steps during the synthesis of human amylin. Several of these steps occur within the amyloid forming region corresponding to residues 20-29. The growing amylin peptide chain is believed to contain secondary structural elements that lead to decreased coupling yields. Single amino acid substitutions in this portion of the amylin amino acid sequence were found to have unexpected and unpredicted beneficial effects on coupling yields. This finding supports our determination that secondary structure of the growing peptide chain affects the efficiency of solid phase synthesis of amylin. We found that coupling yields were maximized using coupling conditions which include use of solvents which optimize swelling of resin (solid support) and those which disrupt secondary structural elements, and minimize formation of intramolecular and intermolecular hydrogen bonds. Use of a capping step after each synthesis cycle (which includes coupling or, optionally, double coupling steps) and selective deprotection of cysteine residues and formation of the intramolecular Cys-Cys disulfide bond while the peptide is still attached to the resin were also discovered to significantly contribute to enhanced yield and purity of the synthetic peptide product.

Thus, in one aspect, the present invention is directed to methods for the solid phase synthesis of amylin or an amylin analog by successively coupling protected amino acids in a predetermined order to give a peptide, under coupling conditions which include conditions disruptive of secondary structure of the growing peptide chain during synthesis. After synthesis of the peptide is complete, the amylin or amylin analog is cleaved from the support. Preferably, an intramolecular disulfide bond between cysteine residues on the peptide is formed before cleaving the peptide from the support.

In one preferred aspect the present invention provides methods for solid phase synthesis of a peptide which comprises amylin or an amylin analog which has enhanced biological activity and is substantially free of deletion and other contaminating peptides wherein said peptide is synthesized using successive synthesis cycles, whereby in each such synthesis cycle, a designated amino acid is added to a growing peptide chain attached to an insoluble resin support by formation of a peptide linkage between an $\alpha$-amino group of the growing peptide chain and on $\alpha$-carboxyl of the designated amino acid; and wherein each synthesis cycle comprises: (a) treating the growing peptide chain under $\alpha$-amino deprotecting conditions to remove an $\alpha$-amino group of the terminal amino acid and generate a free $\alpha$-amino group; (b) activating the $\alpha$-carboxyl group of the $\alpha$-amino protected designated amino acid; (c) contacting the growing peptide chain and the designated amino acid under coupling conditions to form a peptide linkage between the free $\alpha$-amino of the peptide chain and the activated $\alpha$-carboxyl of the designated amino acid; and (d) repeating steps (b) and (c) if the coupling efficiency of step (c) is less than about 97%. It is preferred to repeat steps (b) and (c) if the coupling efficiency is less than about 99%. In another preferred aspect, steps (b) and (c) are repeated in each synthesis cycle. Optionally, the coupling efficiency is measured after each coupling step. Suitable coupling conditions include use of a solvent system which maximizes swelling of the solid support, minimizes secondary structure elements of the peptide chain during synthesis cycles, and minimizes intrapeptide and interpeptide hydrogen bonding. Preferably the synthesis cycle includes a capping step after the coupling step(s) wherein unreacted $\alpha$-amino groups of the peptide chain are rendered unreactive. The synthesis cycle is successively repeated using appropriate protected $\alpha$-amino acids to give amylin or an amylin analog of specified sequence. After completion of the successive synthesis cycles, said amylin or amylin analog is cleaved from the solid support. It is preferred that the cysteine residues of the peptide chain are selectively deprotected and an intramolecular disulfide bond is formed before cleaving the peptide bond from the solid support.

Suitable $\alpha$-amino protective groups include t-butoxycarbonyl and 9-fluorenylmethoxycarbonyl. In one preferred aspect of the methods of the present invention, when t-butoxycarbonyl is used as the $\alpha$-amino protecting group, the $\alpha$-carboxyl groups are activated using dicyclohexylcarbodiimide and 1-hydroxybenzotriazole to form 1-hydroxybenzotriazole enters. A particularly preferred solvent system comprises N-methylpyrrolidone.

The present invention also provides synthetic human amylin produced by solid phase peptide synthesis which has an $EC_{50}$ of about 2.5 nanomoles/liter $\pm 0.3$ log units or less according to an assay of insulin-stimulated incorporation of labelled glucose into glycogen in isolated rat soleus muscle. In an especially preferred aspect, such synthetic human amylin is substantially free of deletion and other contaminating peptides.

The present invention is also directed to amylin or an amylin analog made by our solid phase peptide synthetic procedures as described herein. In one especially preferred aspect, human amylin has an $EC_{50}$ of about 2.5 nanomoles/liter $\pm 0.3$ log units or less according to an assay of insulin-stimulated incorporation of labelled glucose into glycogen in isolated rat soleus muscle.

DEFINITIONS

As used herein, the following terms have the following meanings unless expressly stated to the contrary:

Amylin analogs include non-human amylin species, such as rat amylin and canine amylin, and include peptides and peptide analogs (or mimics) which exhibit amylin-like activity, as measured by assays such as the soleus muscle assay and are chemically and structurally related to native human amylin.

The term to "cap" or "capping" refers to a step in the synthesis cycle in which any free $\alpha$-amino groups of the growing peptide chain bound to the resin support that failed to couple with an activated carboxyl group of the designated $\alpha$-amino protected amino acid are blocked, rendering them unreactive in subsequent synthesis cycles.

"Difficult" couplings or sequences refer to synthesis cycles or sequences which result in undesirably low coupling efficiencies using conventional synthesis cycles with single coupling steps. Difficult sequences are characterized by reproducible stretches of repetitive incomplete aminoacylations (i.e. low coupling efficiencies) and thus, result in lower overall yields.

DETAILED DESCRIPTION OF THE INVENTION

Figure 1:
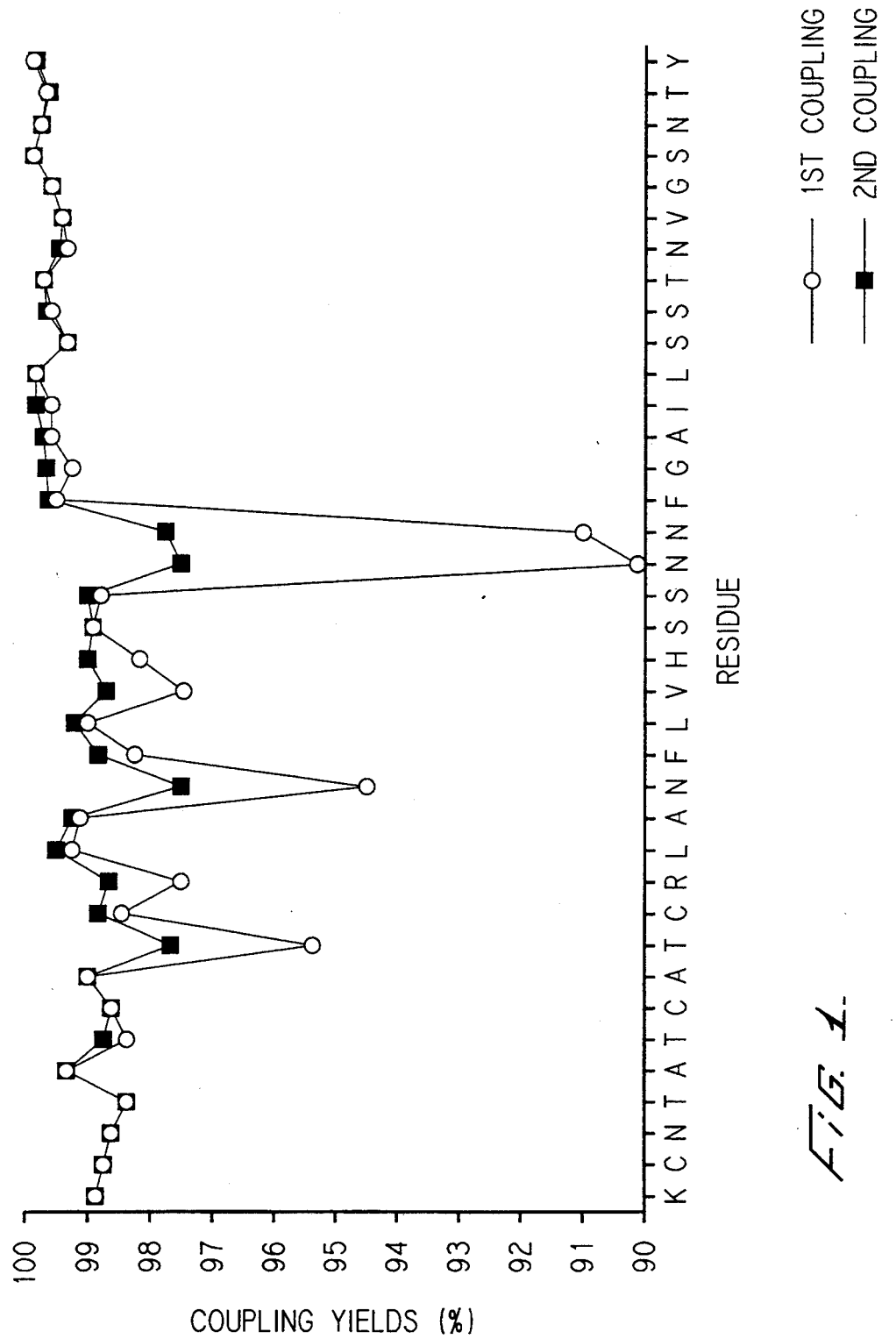
FIG. 1 depicts the coupling yields in a synthesis of human amylin.

Solid phase peptide synthesis is basically the stepwise addition of single amino acids (having protected side-chains and amino termini) to a growing peptide chain, generally proceeding from the carboxy-terminal end to the amino-terminal end, to give a peptide of specified sequence. Protocols for the synthesis of peptides from the amino-terminal end to the carboxy-terminal end have also been developed. Due to instances or racemization and side reactions which may occur when using the amino- to carboxy-terminal synthesis protocols, the carboxy- to amino-terminal synthesis protocols have been preferred.

Typically, using the carboxy- to amino-terminal protocol, solid phase peptide synthesis begins with the covalent attachment of the carboxyl end of an $\alpha$-amino protected first amino acid in the peptide sequence (which will be the carboxy terminal amino acid after the synthesis cycles are completed and the peptide is cleaved from the support), through an organic linker to an insoluble resin support. A general cycle of synthesis comprises deprotection of the α-amino group of the resin-bound amino acid, followed by reaction (coupling) of the free α-amino group with some carboxyl-activated form of the next α-amino protected amino acid to form a peptide linkage and to give a support-bound dipeptide. The synthesis cycle is repeated, adding an amino acid to the growing support-bound peptide chain with each cycle, until the sequence of the support-bound peptide chain is complete. After the synthesis cycles are completed, the link of the peptide to the resin support is cleaved, protecting groups on the sidechains of the individual amino acid residues are removed, the peptide is separated from the support and purified.

Several protocols have been developed for solid phase peptide synthesis which employ differing specified solvent systems, protecting groups (for α-amino groups and for individual amino acid side chains), activated carboxyl groups, resin supports and linkages. (See, e.g., Barany, G., et al., Int. J. Peptide Protein Res. 30:705-738 (1987); Fields, G. B., et al., Int. J. Peptide Protein Res. 35:161-214 (1990); and Kent, S. B. H., Ann. Rev. Biochem. 57:957-89 (1988)).

We believe that the methods of the present invention may be used in conjunction with the various protocols used for solid phase peptide synthesis and may be especially suited for use with automated and semi-automated solid phase peptide synthesis.

In one aspect, the present invention is directed to methods of preparing synthetic amylin using solid state peptide synthesis wherein the peptide produced thereby has a purity of at least about 95% after isolation by preparative reverse phase HPLC (or other chromatographic method such as perfusion), as measured by analytical reverse HPLC or capillary electrophoresis and an $EC_{50}$ of less than about 5 nmoles/liter as measured by soleus muscle assay, as described by Cooper, G. J. S. et al., Proc. Nat'l. Acad. Sci. USA 85:7763-7766 (1988) and Leighton, B. and Cooper, G. J. S., Nature 335:632-635 (1988), the disclosures of which are incorporated herein by reference.

According to the present invention, methods for the chemical synthesis of amylin and amylin analogs are also provided that have uniformly high coupling efficiencies and, thus, generate amylin or amylin analog in enhanced yields and minimize production of deletion peptides which may result, for example, from incomplete synthesis cycles (i.e., synthesis cycles having low coupling efficiencies).

Solid phase synthesis of specified peptides using conventional techniques often results in low yields and/or products of unacceptable purity. Attempts have been made to predict so-called difficult sequences in solid-phase peptide synthesis. However, it has been reported that sequence-related incomplete aminoacylations (couplings) have proven difficult to anticipate and eliminate. (See, e.g., Milton, R. C. def., et al., J. Am. Chem. Soc. 112:6039-6046 (1990)).

In the synthesis of amylin analogs, we have found that one cannot predict which amino acid sequences may prove to yield undesireable coupling efficiencies from one amylin analog to another. Moreover, we have found that a change in only one amino acid in a sequence can result in unpredictable decreases in coupling efficiency and thus lead to impracticability of synthesis.

DESCRIPTION OF THE PREFERRED EMBODIMENTS

According to a preferred aspect of the present invention, we have developed methods for solid phase peptide synthesis of human amylin and of amylin analogs.

According to one preferred aspect, a N-methyl pyrrolidone (NMP) solvent protocol is used to maximize resin swelling and disruption of secondary structural elements. Also according to a preferred aspect, in a synthesis cycle double coupling steps are optionally used if the coupling efficiency of a first coupling step is less than about 97%. More preferably, double coupling steps are used if the coupling efficiency is less than about 99%. Preferably a capping step is used after the coupling step(s) in each synthesis cycle.

Optionally, during the synthesis of the peptide, coupling efficiencies or yields of individual synthesis cycles may be monitored by cleaving the growing peptide chain from the resin support and hydrolyzing the peptide at certain designated points in the synthesis to measure amino acid ratios and test for deletions (or deletion peptides) and incomplete couplings. For example, the growing peptide chain may be hydrolyzed after Gln (10) has been coupled. The ratio of the residues Gln (10), Arg (11), Ile (26), Tyr (37) should be present in the ratio of 1:1:1:1, if the synthesis has proceeded optimally.

Also according to a preferred aspect, Cys-protecting groups are selectively removed and the $Cys_2$-$Cys_7$ disulfide bond is formed before the peptide is cleaved from the support. Attempts to air oxidize amylin under standard conditions (in aqueous solution, pH>8.0) led to a complex mixture of peptides. This is believed to be due to a propensity of amylin to aggregate in solution, thus favoring intermolecular rather than intramolecular disulfide formation. We found it advantageous to cyclize human amylin and amylin analogs while they were bound to the resin (solid support), a procedure which we believe favors intramolecular disulfide bond formation. We found that thallic trifluoroacetate effectively selectively deprotected and oxidized the Acetamidomethyl (Acm) protected cysteine residues of amylin to give cyclized amylin having the $Cys_2$-$Cys_7$ disulfide bond and also removed the α-amino protecting group. The cyclized peptides are then fully deprotected and cleaved with HF in the absence of thiol (or sulfide) scavengers. After following this procedure, no reduced peptide was observed upon analytical reversed phase-HPLC (RP-HPLC) of the crude peptide mixture. The peptides were purified by RP-HPLC using a C-4 reversed phase silica column (10μ) to optimize recovery of peptide from the solid support. Polypropylene tubes were used to collect fractions in order to decrease losses due to adsorption of peptide onto glass tubes.

Synthesis of Human Amylin

By following the procedures disclosed herein (see Example 1), human amylin was synthesized with final synthesis cycle yields (i.e., coupling efficiencies) that averaged 99.1%. Overall coupling efficiencies for each residue were obtained that were greater than or equal to 97.6% (FIG. 1). The quantitative coupling yields were obtained after each synthesis cycle during the solid phase synthesis of human amylin using 4-methylbenzhydrylamine resin (0.72 meq/g) as solid support and using 1-hydroxy-benzotriazole (HOBT)-NMP protocol (Applied Biosystems User's Manual for the ABI 430A Peptide Synthesizer, Version 1.3B, Jul. 1, 1988, section 6, pages 49–70, Applied Biosystems, Inc. (Foster City, Calif.)). Residues which had given satisfactory coupling yields (at least about 99% or greater), as measured by qualitative ninhydrin analysis, during an earlier synthesis of amylin, were single coupled. The remainder of the residues were double coupled to insure enhanced coupling yields. We found that the lowest percent coupling efficiencies were obtained within the sequence of residues 20–29, which corresponds to the amylin forming region. Use of double-coupling cycles for these residues improved the final coupling efficiencies from 90% to 98% and from 91% to 98% for residues 21 and 22 respectively. Other low coupling yields (i.e. those less than or equal to 98.4%) occurred within amylin's proposed alpha-helix region, at residues 9, 14 and 18. (See Table I) Our findings suggest that the low coupling efficiencies encountered during the solid phase synthesis of amylin may result from a propensity of the growing peptide chain to form secondary structural elements that make free amino groups of the growing chain inaccessible to activated amino acids.

HPLC analysis of the crude peptide obtained from this synthesis of amylin using the NMP/dimethylsulfoxide (DMSO)/diisopropylethylamine (DIEA) solvent system and the Applied Biosystems, Inc. (ABI) protocol was less complex (i.e., had fewer peptide components) than that using the dimethylformamide (DMF) solvent system and the ABI protocol. We believe that these advantageous results are due to improved coupling yields by optimizing resin swelling with NMP along with the ability of DMSO and DIEA to disrupt secondary structural elements.

It was recently reported that a HOBT-NMP t-butoxycarbonyl (t-Boc) synthesis gave better average coupling yields for a test peptide containing an amino acid sequence selected to contain the peptide bonds reported to be most difficult to synthesize than a symmetric anhydride-DMF t-Boc synthesis. (Stevens, R. L., et al., abstract, 1990 Protein Society meeting, Aug. 12, 1990, San Diego, Calif.). It has been proposed that sequence-specific coupling difficulties present a particular problem for the 8th through the 16th coupling cycles during a synthesis. (Deber, C. M. et al., Pept. Res. 2:184–188 (1989); Meister, S. M. et al., Peptides, Structure and Function, Proc. 9th Amer. Pept. Symp. (Deber, C. M. et al. Eds., Pierce Chemical Co., Rockford, Ill.), pages 103–107 (1985)); Kent, S. B. H. et al., Synthetic Peptides in Biology and Medical (Alitalo, K., et al. Eds., Elsevier Science Publishers, B. V. Biomedical Division), pages 29–56 (1985)). However, during our synthesis of amylin, we found there to be no low yield couplings in this region, whereas there were such couplings in cycles 17 to 28. (See FIG. 1).

It has been proposed that use of resins with lower substitution of anchored amino acid improves coupling yields for less effective couplings. (See, Milton et al., J. Am. Chem. Soc. 112:6039–6045 (1990)). However, in our study of the sequence dependence of difficult coupling sites, we have synthesized human amylin using a resin solid support with a lower substitution of anchored amino acid and have synthesized certain amylin analogs. We found that decreasing the substitution of the resin from 0.72 meq/g to 0.44 meq/g did not significantly improve coupling yields at several residues which we had found in previous syntheses to have lower coupling yields. (See Table I). We believe that these findings show that the apparent inaccessibility of the free amino group of the growing peptide chain for these couplings is due to intramolecular rather than intermolecular aggregation of resin-bound peptides.

Synthesis of Canine Amylin and Amylin Analogs

Canine amylin was synthesized using the same synthesis protocol as used for synthesis of human amylin. Canine amylin contains four amino acid changes from the sequence of human amylin. In canine amylin, the eighteenth residue is arginine, the nineteenth residue is threonine, the twenty-third residue is leucine, and the twenty-ninth residue is proline. Surprisingly, we found that the synthesis of canine amylin proceeded with higher coupling efficiencies than those we had obtained during the synthesis of human amylin. The differences in coupling yields were especially surprising at certain coupling steps that we had found with human amylin to give a lower yield. For example, residue 21 in canine amylin gave an initial coupling efficiency as 99.7% compared to 90.1% for residue 21 in human amylin. See Table I.

Two human amylin analogs were synthesized which contained single amino acid changes found in the canine amylin sequence. We found that these changes dramatically affected coupling yields at several other individual residues. See Table I. We found that substitution of proline for $^{29}$serine improved final coupling efficiencies at residues 9, 18, 21 and 22. Also, we found that substitution of leucine for $^{23}$phenylalanine resulted in increased coupling efficiencies for residues 21 and 22. These sequence changes resulted in some unanticipated decreases in coupling efficiencies. For example, during the synthesis of $^{29}$[Pro]human amylin, a single coupling of residue 8 gave a yield of 80.8%.

Due to the unpredictable effect of conservative amino acid substitutions that we have found on coupling yields, it is preferred to use synthesis cycles having double-coupling steps during the synthesis of amylin analogs. Our findings that these sequence changes can have a surprisingly significant effect on coupling efficiencies are further support that low yield couplings in the synthesis of amylin may be due to intramolecular interactions of the growing amylin peptide chain.

Peptide Synthesis Procedures

The solvents, amino acid derivatives and 4-methylbenzyhydrylamine resin (0.72 meq/g) used in the peptide synthesizer were purchased from Applied Biosystems, Incorporated, unless otherwise indicated. Boc-His(BOM) was purchased from Bachem Incorporated. Boc-Cys(Acm) and 4-methylbenzyhydrylamine resin (0.44 meq/g) were obtained from Peninsula Laboratories. Thallic trifluoracetate was purchased from Eastman Kodak. Anisole, dimethylsulfide and formic acid were obtained from Aldrich Chemical Company. Air Products supplied the HF. Ethyl ether, acetic acid and ethanol were purchased from Fisher Scientific.

Solid phase peptide synthesis was carried out on an Applied Biosystems Incorporated 430A automatic synthesizer using Option 1/NMP-HOBt t-Boc Chemistry (Applied Biosystems User's Manual for the ABI 430A Peptides Synthesizer, Version 1.3B (Jul. 1, 1988), Section 6, pages 49–70, Applied Biosystems, Inc., Foster City, Calif.). Capping was done and resin samples (4.7 to 8.6 mg) were collected after every coupling cycle, washed with methanol and methylene chloride, vacuum dried and weighed. Quantitative coupling yields were obtained using a standard protocol (Sarin, V. K., et al., Anal. Biochem. 117:147–157 (1981)). Peptide-resins were cleaved with HF (−5° C. to 0° C., 1 h). HF was removed by positive nitrogen flow followed by vacuum. Cleaved peptide was washed with ether in a sintered glass funnel and allowed to dry overnight under atmospheric conditions. The peptide was extracted from the resin with alternating water and acetic acid, and the filtrates were lyophilized. Prior to purification, peptide solutions were filtered using MSI nylon filters (0.45μ, MSI, Westboro, Mass.). High performance liquid chromatography (preparative and analytical) was carried out on a Waters Delta Prep 3000 system equipped with a Spectra-Physics ChromJet integrator. A Vydac C-4 preparative column (10 μ, 2.2×25 cm) was used to isolate peptides, and purity was determined using a Vydac analytical column (5μ, 0.46×25 cm). Solvents (A=0.1% TFA/water and B=0.1% TFA/ACN) were delivered to the analytical column at a flowrate of 1.0 or 1.3 ml/min and to the preparative column at 15 or 20 ml/min. Purity was also determined with a DIONEX Capillary Electrophoresis System I operating at 20,000 volts, using gravity injection, 20 mM citrate buffer (pH 2.5), with a 67 cm capillary and monitoring at 214 nm. Electropherograms were processed and analyzed using the Waters MAXIMA program. Amino acid analysis were performed on the Waters Pico.Tag system and processed using the Maxima program. The peptides were hydrolyzed by vapor-phase acid hydrolysis (115° C., 20–24 h). Hydrolysates were derivatized and analyzed in a standard fashion (Pico.Tag Workstation Operator's Manual and the Pico.Tag Method Manual, Walters). Fast atom bombardment analysis was carried out by M-Scan, Incorporated (West Chester, Penn.). Mass calibration was performed using cesium iodide or cesium iodide/glycerol.

To assist in understanding the present invention, the following examples which include the results of a series of experiments are set forth. The following examples relating to this invention are illustrative and should not, of course, be construed as specifically limiting the invention. Moreover, such variations of the invention, now known or later developed, which would be within the purview of one skilled in the art are to be considered to fall within the scope of the present invention as hereinafter claimed.

EXAMPLES

EXAMPLE 1

Preparation of Human Amylin (I)

Human Amylin was assembled on 4-methylbenzyhydrylamine resin (0.69 g, 0.72 meq/g, 0.5 mmol) using Boc-protected amino acids from ABI including Boc-Arg(Tos). Double-coupling cycles were used throughout the synthesis with the exception of residues 2, 5, 8, 28, and 32–37 which were single-coupled, and the synthesis was completed furnishing $^{1-37}$Human Amylin-resin (1.79 g).

EXAMPLE 2

Preparation of Human Amylin (II)

Human Amylin was synthesized as described for synthesis of Example 1 with the following exceptions: 4-methylbenzyhydrylamine (1.14 g, 0.44 meq/g, 0.5 mmol) and Boc-Arg(Mts) were used in the synthesis, and only double-coupling cycles were used. Peptide-resin (0.52 g) was removed after the 13th coupling cycle, and the synthesis was completed furnishing $^{1-37}$human Amylin-resin (2.26 g). A portion of the completed resin (0.96 g, 0.12 mmol, 1.0 equiv) was stirred with anisole (1 ml), TFA (21 ml) and thallic trifluoracetate (0.079 g, 0.15 mmol, 1.3 equiv) for 1 hour at −4° C. to 0° C. Cold ether was added and the mixture was filtered through a sintered glass funnel. The resin was washed with ether and allowed to dry. The oxidized peptide-resin was deprotected and cleaved with HF (10 ml) in the presence of anisole (1 ml) and DMS (1 ml). Extraction and lyophilization of the extracts furnished fluffy white peptide (0.357 g). A portion of the peptide (0.099 g) was dissolved in guanidine:HCl (6M, 10 ml) and purified on the preparative column (20 ml/min, 20% B for 15 min., 20–28% B over 1 min., 28–31% B over 30 min.) and the fractions were collected in borosilicate tubes. Purity of fractions was determined isocratically using the analytical column (30% B). Fractions were pooled according to RP-HPLC purity, furnishing white peptide (95% pure fractions, 1.7 mg and 85–95% pure fractions, 6.19 mg). Additional peptide (231 mg) was similarly purified in three additional preparative runs. Material of highest purity obtained from the four purifications was pooled to yield Human Amylin (>95% pure, 6.64 mg). Capillary electrophoresis indicated a purity of 92.3%. Amino acid analysis (6M HCl, 115°): Ala, 3.94; Arg, 0.88; Asx, 6.10; Glx, 1.06; Gly, 1.96; His, 0.89; Ile, 1.06; Leu, 2.98; Lys, 0.99; Phe, 2.12; Ser, 5.13; Thr, 4.96; Tyr, 1.08; Val. 1.95. FAB Mass Spectrometry: $(M+H)^+$ Calc. 3904.32; $(M+H)^+$ Found: 3904.84.

Example 3

Preparation of Canine Amylin

Canine amylin was synthesized as described for human amylin in Example 1 with the following exceptions: Boc-Arg(Mts) was used and double couplings were performed only for residues 9, 10, 15, 16, 17, 20, 21, 23, 24, 27, 29, and 29. The synthesis gave 3.03 g of peptide-resin. Canine amylin peptide-resin (0.25 g) was cyclized and cleaved as described for the human amylin synthesis of Example 2. The peptide (51 mg) was dissolved in water (5 ml), and the pH of the solution was adjusted to 8 with ammonium carbonate to reverse any N to O-acetyl shifts due to HF conditions. The peptide was purified by RP-HPLC (20 ml/min., 30–38% B over 40 min.). Peptide fractions of similar purity were pooled together and lyophilized to give granular white peptide (98–99% pure fractions, 2.12 mg). Analytical RP-HPLC (30–37% B over 40 min.) indicated a purity of 98%. Capillary electrophoresis indicated a homogeneous product. Amino acid analysis (6M HCl, 115°). Ala, 4.27; Arg, 1.87; Asx, 6.28; Glx, 0.81; Gly, 2.12; Ile, 0.97; Leu, 4.11; Lys, 0.91: Phe, 1.31; Pro, 0.87; Ser, 3.17; Thr, 6.09; Tyr, 1.23; Val, 1.98. FAB Mass Spectrometry: $(M+H)^+$ Calc. 3913; $(M+H)^+$ Found:3913.

Example 4

Preparation of $^{23}$Leu-Human Amylin $^{23}$Leu-Human Amylin was synthesized as described for the human amylin synthesis of Example 2 to furnish peptide-resin (2.439 g). A portion of the peptide-resin (1.0 g) was cyclized, cleaved, deprotected and extracted in the same fashion as described for the human amylin synthesis of Example 2 to yield fluffy, white peptide (0.372 g). Most of the crude peptide (0.348 g) was dissolved in guanidine.HCl (6M, 15 ml) and diluted with aqueous HCl (3 mM, 10 ml). The filtered peptide solution was applied to the preparative column in 5 ml aliquots followed by 10 minute washes with 5% B. The peptide was purified by RP-HPLC (15 ml/min., 5% B for 15 min., 5–28% B over 10 min. 28% B for 10 min, 28–31% B over 30 min.), to yield white peptide (14 mg). Capillary electrophoresis indicated a purity of 96.1%. Amino acid analysis (6 M HCl, 115°): Ala, 3.71; Arg, 0.87; Asx, 5.65; Glx, 0.62; Gly, 2.23; His, 0.95; Ile, 1.07; Leu, 4.14; Lys, 1.20; Phe, 0.96; Ser, 5.25; Thr, 5.28; Tyr, 1.10: Val, 1.95. FAB Mass Spectrometry: $(M+H)^+$ Calc. 3870.31: $(M+H)^+$ Found 3869.64.

Example 5

Preparation of $^{29}$Pro-Human Amylin $^{29}$Pro-Human Amylin was synthesized as described for the human amylin synthesis of Example 2 except that single-coupling cycles were used for residues 1–8, 12–13, 16, 19–20, and 23–37. Resin (0.27 g) was removed after the 16th cycle and the synthesis was completed to furnish $^{29}$Pro-Human Amylin (2.04 g). A portion of the resin (1 g) was oxidized and cleaved, as described for the human amylin synthesis of Example 2, to furnish crude peptide (0.339 g). Some of the peptide (0.330 g) was dissolved in guanidine.HCl (6M) and aqueous HCl (3 mM) and was filtered through a glass-wool stoppered Pasteur pipet before being passed through a nylon filter. Residual peptide on the glass-wool was eluted with formic acid, filtered through the nylon filter and added to the guanidine and HCl filtrates to give a final volume of about 100 ml. The peptide solution was applied to the column in 10 to 15-ml aliquots followed by 10 min. washes with 5% B. The peptide was purified (15 ml/min., 5% B for 15 min., 5–25% B over 10 min., 25% B for 25 min., 25–26% B over 5 min., 26% B for 5 min., 26–27% B over 5 min., 27% B for 15 min., 27–28% B over 5 min., 28% B for 15 Min. 28–29% B over 5 min., 29% B for 15 min.) and fractions of similar purity were prepared and lyophilized to give white fluffy peptide (93% pure, 7.56 mg). Capillary electrophoresis indicated a purity of 91.4%. Amino acid analysis (6M HCl, 115°). Ala, 4.62; Arg, 0.93; Asx, 5.66; Glx, 0.87; Gly, 2.22; His, 0.94; Ile, 1.00; Leu, 2.95; Lys, 0.87; Phe, 2.08; Pro, 1.06; Ser. 4.03; Thr. 5.02; Tyr, 1.11; Val. 2.06. FAB Mass Spectrometry: $(M+H)^+$ Calc. 3914.36; $(M+H)^+$ Found 3913.57.

TABLE I

Coupling yields for human amylin and analogues

| Residue Coupling Yields (%) | Peptide: Human (0.72 meq/g) 1st, 2nd | Human (0.44 meq/g) 1st, 2nd | Canine 1st, 2nd | $^{23}$Leu-Human 1st, 2nd | $^{29}$Pro-Human 1st, 2nd |
|---|---|---|---|---|---|
| $^8$Ala | 99.0, Na$^a$ | 99.5, 99.5 | 99.7, NA | ND$^b$, ND | 80.8, NA |
| $^9$Thr | 95.5, 97.8 | 99.2, ND | ND, ND | ND, ND | 98.8, 98.8 |
| $^{13}$Ala | 99.2, 99.3 | 99.2, 99.4 | ND, ND | 98.4, 99.7 | 94.7, NA |
| $^{14}$Asn | 94.5, 97.7 | 97.1, ND | 97.1, 99.6 | ND, 99.7 | 92.2, 96.8 |
| $^{18}$His | 98.4, 99.0 | ND, 99.4 | 99.6, 99.8 | ND, 99.7 | 99.4, 99.5 |
| $^{21}$Asn | 90.1, 97.6 | 90.1, 98.0 | 99.7, 99.8 | 98.4, 99.7 | 99.6, ND |
| $^{22}$Asn | 91.1, 97.8 | 88.3, 98.1 | 99.5, 99.7 | 95.0, ND | 99.5, 99.6 |

$^a$NA: not applicable, refers to residues which were not double-coupled.
$^b$ND: not determined, refers to coupling yields which were not quantitated.

We claim:

1. Synthetic human amylin produced by solid phase peptide synthesis having an $EC_{50}$ of about 2.5 nanomoles/liter±0.3 log units or less according to an assay of insulin-stimulated incorporation of labelled glucose into glycogen in isolated rat soleus muscle.

2. Synthetic human amylin according to claim 1 which is substantially free of deletion and other contaminating peptides.

3. A method for solid phase synthesis of amylin or an amylin analog which has an $EC_{50}$ of about 2.5 nanomoles/liter±0.3 log units or less and is substantially free of deletion and other contaminating peptides which comprises (a) successive synthesis cycles wherein, in each cycle, a protected designated amino acid is covalently coupled to a growing peptide chain covalently linked to an insoluble solid resin support to give a peptide having an additional amino acid, under coupling conditions, wherein said coupling conditions include use of a N-methyl pyrrolidone solvent system for said coupling cycles which maximizes swelling of said resin support, minimizes secondary structure elements of the peptide chain during synthesis, and minimizes intrapeptide and interpeptide hydrogen bonding, and wherein, if initial coupling of amino acid to each peptide chain in a synthesis cycle is less than about 97%, a second coupling step is performed in the synthesis cycle; (b) a capping step after each synthesis cycle and before the next synthesis cycle wherein unreacted deprotected α-amino groups on the growing peptide chain are reacted to block further chain extension; (c) selectively deprotecting cysteine residues and forming an intramolecular disulfide bond between cysteine residues on the peptide chain before cleaving the peptide chain from the solid support; and (d) cleaving said amylin or amylin analog from said solid support.

4. A method according to claim 3 wherein said second coupling step is performed if initial coupling is less than about 99%.

5. A method for solid phase synthesis of a peptide which comprises amylin or an amylin analog which has an $EC_{50}$ of about 2.5 nanomoles/liter±0.3 log units or less and is substantially free of deletion and other contaminating peptides wherein said peptide is synthesized using successive synthesis cycles whereby in each such synthesis cycle a designated amino acid is added to a growing peptide chain attached to an insoluble resin support by formation of a peptide linkage between an α-amino group of the peptide chain and an α-carboxyl of the designated amino acid wherein each synthesis cycle comprises:

(a) treating the growing peptide chain under α-amino deprotecting conditions to remove an α-amino protecting group from the α-amino group of the terminal amino acid and generate a free α-amino group;

(b) activating the α-carboxyl group of the α-amino protected designated amino acid;

(c) contacting said growing peptide chain and said designated amino acid under coupling conditions to form a peptide linkage between the free α-amino of the peptide chain and the activated α-carboxyl of the designated amino acid wherein said coupling conditions include use of a N-methyl pyrrolidone solvent system which maximizes swelling of the resin support, minimizes formation of secondary structure of the peptide chain during synthesis and minimizes intrapeptide and interpeptide hydrogen bonding;

(d) measuring the coupling efficiency of step (c);

(e) if the measured coupling efficiency of step (c) is less than about 97%, repeating steps (b) and (c);

(f) capping unreacted free α-amino groups of the peptide chain to render them unreactive;

(g) repeating said synthesis cycle of steps (a) to (f) using the appropriate designated amino acids to give amylin or any amylin analog of a specific sequence;

(h) upon completion of said successive synthesis cycles selectively deprotecting cysteine residues of the peptide and forming an intramolecular disulfide bond between the cysteine residues before cleaving the peptide from the support; and (i) cleaving said amylin or amylin analog from said solid support.

6. A method according to claim 5 wherein steps (b) and (c) are repeated if the coupling efficiency of step (c) is less than about 99%.

7. A method for solid phase synthesis of a peptide which comprises amylin or an amylin analog which has an $EC_{50}$ of about 2.5 nanomoles/liter±0.3 log units or less and is substantially free of deletion and other contaminating peptides wherein said peptide is synthesized using successive synthesis cycles, whereby in each such synthesis cycle, a designated amino acid is added to a growing peptide chain attached to an insoluble resin support by formation of a peptide linkage between an α-amino group of the growing peptide chain and an α-carboxyl of the designated amino acid; and wherein each synthesis cycle comprises:

(a) treating the growing peptide chain under α-amino deprotecting conditions to remove an α-amino group of the terminal amino acid and generate a free α-amino group;

(b) activating the α-carboxyl group of the α-amino protected designated amino acid;

(c) contacting said growing peptide chain and said designated amino acid under coupling conditions to form a peptide linkage between the free α-amino of the peptide chain and the activated α-carboxyl of the designated amino acid wherein said coupling conditions include use of a N-methyl pyrrolidone solvent system which maximizes swelling of said resin support, minimizes secondary structure elements of the peptide chain during synthesis cycles and minimizes intrapeptide and interpeptide hydrogen bonding;

(d) if coupling efficiency of step (c) is less than about 97%, repeating steps (b) and (c);

(e) capping unreacted free α-amino groups of the peptide chain to render them unreactive;

(f) repeating said synthesis cycle of steps (a) to (e) using appropriate designated amino acids to give amylin or an amylin analog of specified sequence;

(g) upon completion of all said synthesis cycles selectively deprotecting cysteine residues of the peptide chain and forming an intramolecular disulfide bond between the cysteine residues before cleaving the peptide chain from the support; and (h) cleaving said amylin or amylin analog from said solid support.

8. A method according to claim 7 wherein steps (b) and (c) are repeated if the coupling efficiency of step (c) is less than about 99%.

9. A method for solid phase synthesis of a peptide which comprises amylin or an amylin analog which has an $EC_{50}$ of about 2.5 nanomoles per liter±0.3 log units or less and is substantially free of deletion and other contaminating peptides wherein said peptide is synthesized using successive synthesis cycles, a designated amino acid is added to a growing peptide chain attached to an insoluble resin support by formation of a peptide linkage between an α-amino group of the growing peptide chain and α-carboxyl of the designated amino acid; and wherein each synthesis cycle comprises:

(a) treating the growing peptide chain under α-amino deprotecting conditions to remove an α-amino group of the terminal amino acid and generate a free α-amino group;

(b) activating the α-carboxyl group of the α-amino protected designated amino acid;

(c) contacting said growing peptide chain and said designated amino acid under coupling conditions to form a peptide linkages between the free α-amino of the peptide chain and the activated α-carboxyl of the designated amino acid;

(d) repeating steps (b) and (c); and (e) capping unreacted free α-amino groups of the peptide chain to render them unreactive; and after completion of all synthesis cycles;

(f) selectively deprotecting cysteine residues of the peptide and forming an intramolecular disulfide bond between the cysteine residues before cleaving the peptide from the support; and (g) cleaving said amylin or amylin analog from said solid support.

10. A method for the solid phase synthesis of amylin or an amylin analog having an $EC_{50}$ of about 2.5 nanomoles/liter±0.3 log units or less which comprises successively coupling protected amino acids in a predetermined order to a growing peptide chain covalently attached to a solid support to give a peptide, under coupling conditions which include N-methyl pyrrolidone solvent conditions substantially disruptive of secondary structure of the growing peptide chain during synthesis; upon completion of successive coupling, forming an intramolecular disulfide bond between cysteine residues on the peptide before cleaving the peptide from the solid support; and cleaving said amylin or said amylin analog from said solid support.

11. Amylin or an amylin analog produced according to the process of any of claims 3, 5, 7, 9 or 10.

12. Amylin or an amylin analog according to claim 11 having an $EC_{50}$ of about 2.5 nanomoles/liter±0.3 log units or less according to an assay of insulin stimulated incorporation of labelled glucose into glycogen in isolated rat soleus muscle.

* * * * *